(12) United States Patent  (10) Patent No.: US 8,318,097 B2
Stöcklinger  (45) Date of Patent: Nov. 27, 2012

(54) APPARATUS FOR EXTRACTING GASEOUS SPECIMENS TO BE MEASURED FROM A PRODUCTION PROCESS AND SYSTEM

(75) Inventor: Robert Stöcklinger, Feldkirchen-Westerham (DE)

(73) Assignee: G+R Technology Group AG, Regenstauf (DE)

( * ) Notice: Subject to any disclaimer, the term of this patent is extended or adjusted under 35 U.S.C. 154(b) by 488 days.

(21) Appl. No.: 12/581,585

(22) Filed: Oct. 19, 2009

(65) Prior Publication Data

US 2011/0058987 A1  Mar. 10, 2011

(30) Foreign Application Priority Data

Sep. 4, 2009 (DE) .................. 10 2009 043 947

(51) Int. Cl.
*G01N 33/00* (2006.01)
(52) U.S. Cl. ............ 422/78; 422/50; 422/68.1; 422/500
(58) Field of Classification Search .................. 422/50, 422/78, 68.1, 500
See application file for complete search history.

(56) References Cited

U.S. PATENT DOCUMENTS

| | | | |
|---|---|---|---|
| 4,118,987 A | 10/1978 | Zeh | |
| 4,272,481 A | 6/1981 | Ahlstrom et al. | |
| 4,580,452 A | 4/1986 | Masson | |
| 4,688,436 A | 8/1987 | Richon et al. | |
| 4,873,876 A | 10/1989 | Sheridan et al. | |
| 4,887,472 A | 12/1989 | Jansen | |
| 5,005,432 A | 4/1991 | Faulkner | |
| 5,191,211 A | 3/1993 | Gorman | |
| 5,747,708 A | 5/1998 | Weiberth | |
| 6,153,149 A | 11/2000 | Rabitz et al. | |
| 6,227,034 B1 | 5/2001 | Trochesset | |
| 2004/0099143 A1 | 5/2004 | Welker | |
| 2004/0131528 A1 | 7/2004 | Kendig et al. | |
| 2008/0267834 A1 | 10/2008 | Kim et al. | |
| 2009/0004090 A1 | 1/2009 | Kim et al. | |

FOREIGN PATENT DOCUMENTS

| | | |
|---|---|---|
| DE | 2302899 | 7/1974 |
| DE | 3932202 A1 | 4/1991 |
| DE | 9401379 U1 | 11/1994 |
| DE | 29800967 U1 | 4/1998 |
| GB | 2000590 A | 1/1979 |

OTHER PUBLICATIONS

International Search Report mail Oct. 4, 2010 from PCT/EP2010/059989 filed Jul. 12, 2010.

*Primary Examiner* — Sam P Siefke

(74) *Attorney, Agent, or Firm* — Patentbar International PC

(57) ABSTRACT

An apparatus and a system for extracting gaseous specimens to be measured, preferably during the production of polycrystalline silicon, are disclosed. The apparatus according to the invention is a flange-like device (80), which is placed between each of the at least two pipe sections (11*a*, 11*b*, 21*a*, 21*b*, 41*a*, 41*b*) of the outlet pipes (11, 21, 41).

3 Claims, 5 Drawing Sheets

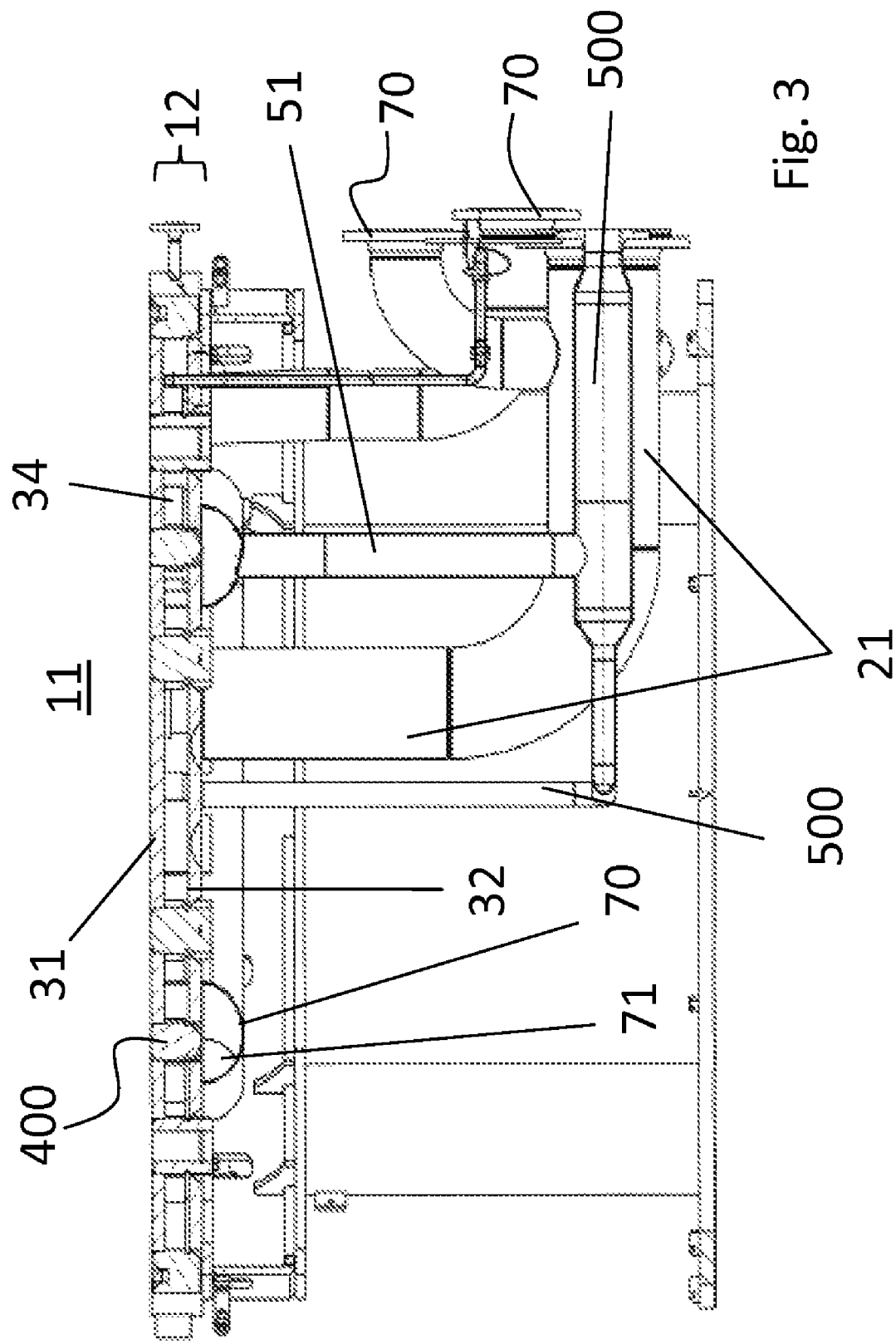

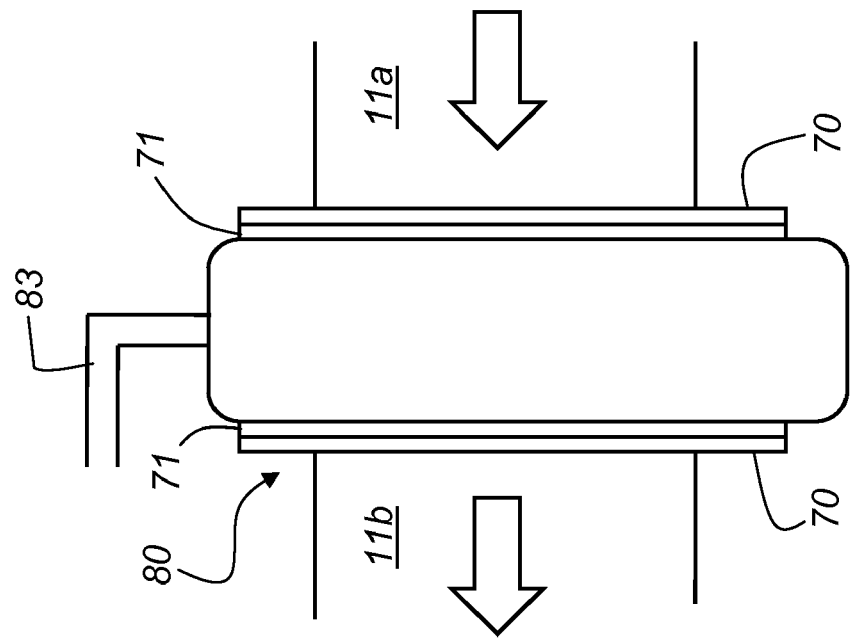
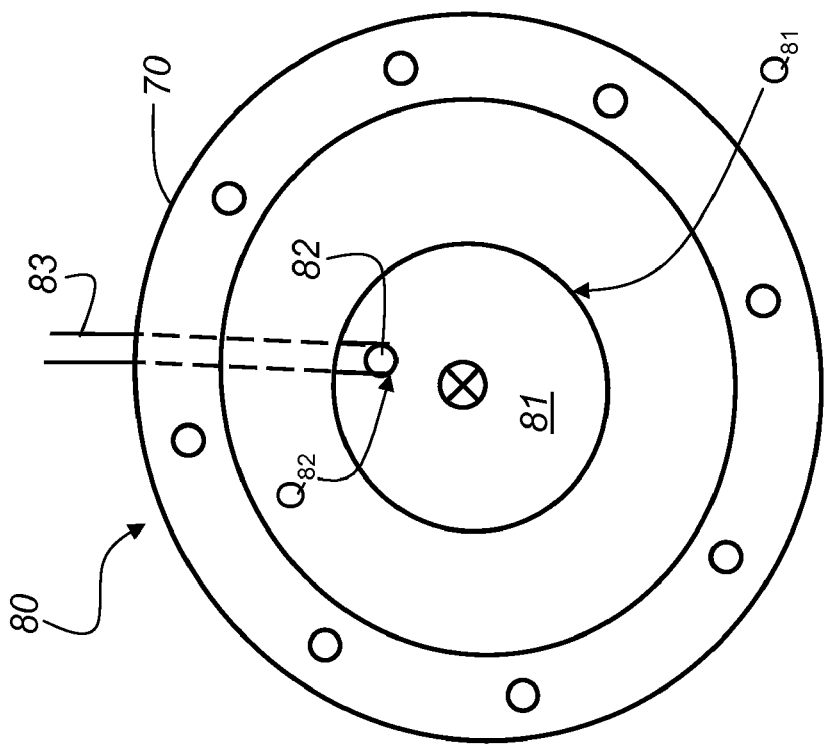

APPARATUS FOR EXTRACTING GASEOUS SPECIMENS TO BE MEASURED FROM A PRODUCTION PROCESS AND SYSTEM

RELATED APPLICATIONS

This application claims priority to German Patent Application No. 10 2009 043 947.1, filed on Sep. 4, 2009, which is incorporated herein by reference in its entirety.

FIELD OF THE INVENTION

The present invention relates to an apparatus for extracting gaseous specimens to be measured from a production process.

Furthermore, the invention relates to a system for the production of polycrystalline silicon.

BACKGROUND OF THE INVENTION

The polycrystalline silicon can be produced according to the monosilane process or the Siemens process. The apparatus according to the invention can also be used with both methods. The methods substantially differ in the reaction partners, with which the polycrystalline silicon is produced. In the Siemens process, trichlorosilane ($SiHCl_3$) is thermally decomposed in presence of hydrogen on heated high-purity silicon rods at 1000 to 2000° C. The pure silicon is thereby deposited onto the rods. The hydrogen chloride released in the process is fed back into the production. The process takes place at a pressure of approximately 6.5 bar.

In the monosilane process, monosilane ($SiH_4$) is thermally decomposed in presence of hydrogen on heated high-purity silicon rods at 850 to 900° C. The pure silicon grows is thereby deposited onto the rods. The monosilane process takes place at a pressure of approximately 2 to 2.5 bar.

SUMMARY OF THE INVENTION

The object of the invention is to create an apparatus with which gaseous specimens to be measured are extracted for analysis during the running process in a simple way.

The above object is achieved by an apparatus for extracting gaseous specimens to be measured from a running production process. The apparatus comprises at least one reactor. A pipe system is provided for feeding and/or discharging the at least one reactor with reaction gas. The pipe system has at least a first pipe section and a second pipe section. A flange connects the first pipe section and the second pipe section. The inventive apparatus is designed as a flange-like device and is placed between the first pipe section and the second pipe section of the pipe system.

Furthermore, is an object of the invention to provide a system for the production of polycrystalline silicon.

The above object is achieved by a system which comprises at least one reactor, at least one converter, at least one injection tank and at least one vaporizer.

It is of particular advantage, if the apparatus is a flange-like device. Thereby, the flange-like device is placed between each of the at least two pipe sections of the pipe system. A pipe is connected with each reactor for the supply and discharge of a mixture of gases. An outlet pipe is provided with each converter for the discharge of a mixture of gases. An outlet pipe is provided with each vaporizer for the discharge of a mixture of gases. The pipes, used in the system have a first pipe section and a second pipe section. Flanges are used to connect and to separate the first pipe section and the second pipe section. A flange-like device for withdrawing the specimens to be measured is placed between the first pipe section and the second pipe section of the reactor, of the converter and/or of the vaporizer respectively.

The flange-like device is provided with a pipe section for the passage of mixtures of gases. A sampling element interferes with the passage. It is of particular advantage, that the sampling element is a pipe having a circular cross-section which is significantly smaller than the cross-section of the pipe section for the pipe of the mixture of gases. The opening of the sampling element points thereby in the direction from where the mixture of gases comes from. Each flange-like device intended for the sample withdrawing is provided in each case with a pipe. These pipes lead to a gas-phase chromatograph, in which the gases coming in each case from the individual sampling stations can be analyzed. The pipes, which lead to the gas-phase chromatograph, are heated.

The apparatus according to the invention is adapted for the usage with the production process for the production of polycrystalline silicon. The system for the production of polycrystalline silicon comprises at least one reactor, at least one converter, at least one injection tank and at least one vaporizer. Each reactor has a pipe system which is provided with an inlet pipe and an outlet pipe for mixtures of gases. Likewise, each converter is provided with an outlet pipe for the mixture of gases. The vaporizer also comprises an outlet pipe for the mixture of gases. All outlet pipes consist of at least two pipe sections, which are in each case connected with flanges.

It is obvious for a person skilled in the art that the system for the production of polycrystalline silicon has a plurality of individual elements, such as the reactor, the vaporizer and/or the converter. The number and combination of the individual elements conforms finally with the demands of the customer.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 3 shows a lateral view of the reactor base, in which one looks laterally onto the inlet pipes and outlet pipes for the reactor base.

FIG. 4 shows a view of the device according to the invention in direction of flow of the mixture of gases, in which a sampling element is placed in the gas passage.

FIG. 5 shows a schematic lateral view of the device according to the invention, which is placed between two pipe sections.

DETAILED DESCRIPTION OF THE PREFERRED EMBODIMENTS

Same reference numbers refer to same elements throughout the various figures. Furthermore, only reference numbers necessary for the description of the respective figure or for placing the figure into the context of other figures are shown in the individual figures for the sake of clarity. The following description refers to the production procedure of polycrystalline silicon according to the monosilane process. However, this description presents only one example of using the apparatus according to the invention and should consequently not be regarded as limiting the invention.

Figure 1:
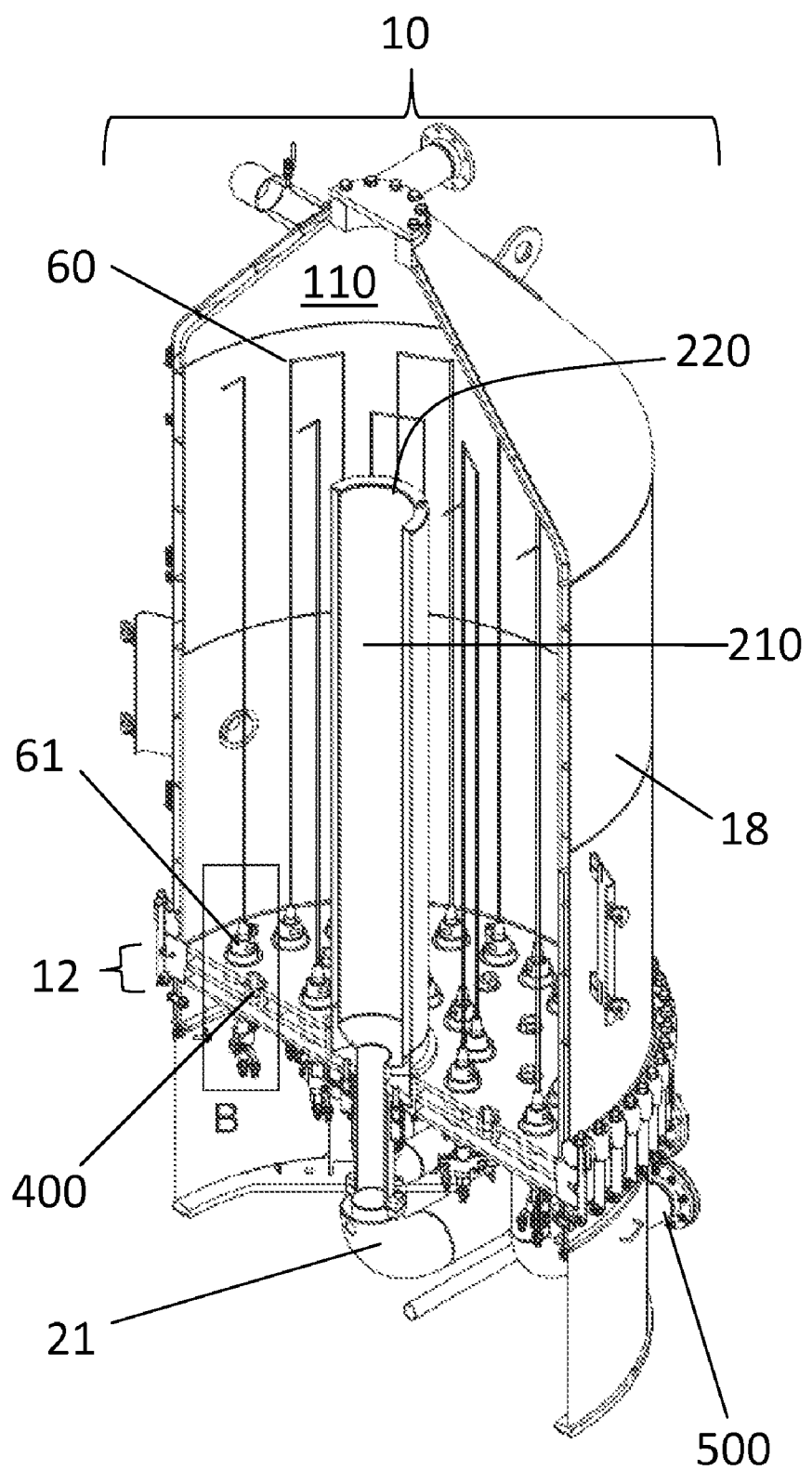
FIG. 1 shows a perspective sectional view of a reactor for the production of polycrystalline silicon according to the prior art.

FIG. 1 shows a reactor 10 for the production of polycrystalline silicon according to the prior art. The reactor base 12 is provided with a plurality of nozzles 400, through which monosilane enters the interior space 110 of the reactor 10. Likewise, a plurality of filament rods 60 is placed on the reactor base 12, which cut off the polycrystalline silicon from the monosilane during the process. In the embodiment shown here, an outlet pipe 21 is provided for the gas from the interior space 110 of the reactor. The outlet pipe 21 for the gas from the interior space 110 of the reactor 10 is an inner pipe 210 with a gas inlet 220, through which the abstracted monosilane is discharged for enhancement and/or further processing. The gas inlet 220 of the inner pipe 210 is thereby clearly spaced from the reactor base 12. This is necessary so that it is ensured that fresh monosilane which has entered the interior space 110 of the reactor 10 does not escape immediately through the gas inlet 220 for abstracted monosilane. The reactor wall 18 and the inner pipe 210 are double-walled and can thereby be cooled with water. The inner pipe 210 is lead through the reactor base 12. The abstracted monosilane is lead for enhancement and/or further processing with the outlet pipe 21. A feeding pipe 500 for fresh monosilane is also provided at the reactor base 12. This feeding pipe 500 ends in the multilayered constructed reactor base 12. From there, the monosilane is distributed on the various nozzles 400 within the reactor base and reaches then the interior space 110 of the reactor 10. The nozzles 400 and the filament rods 60 which are placed in the respective mountings 61 are arranged in the same way about the inner pipe 210 which is positioned in the center of the reactor base 12.

Figure 2:
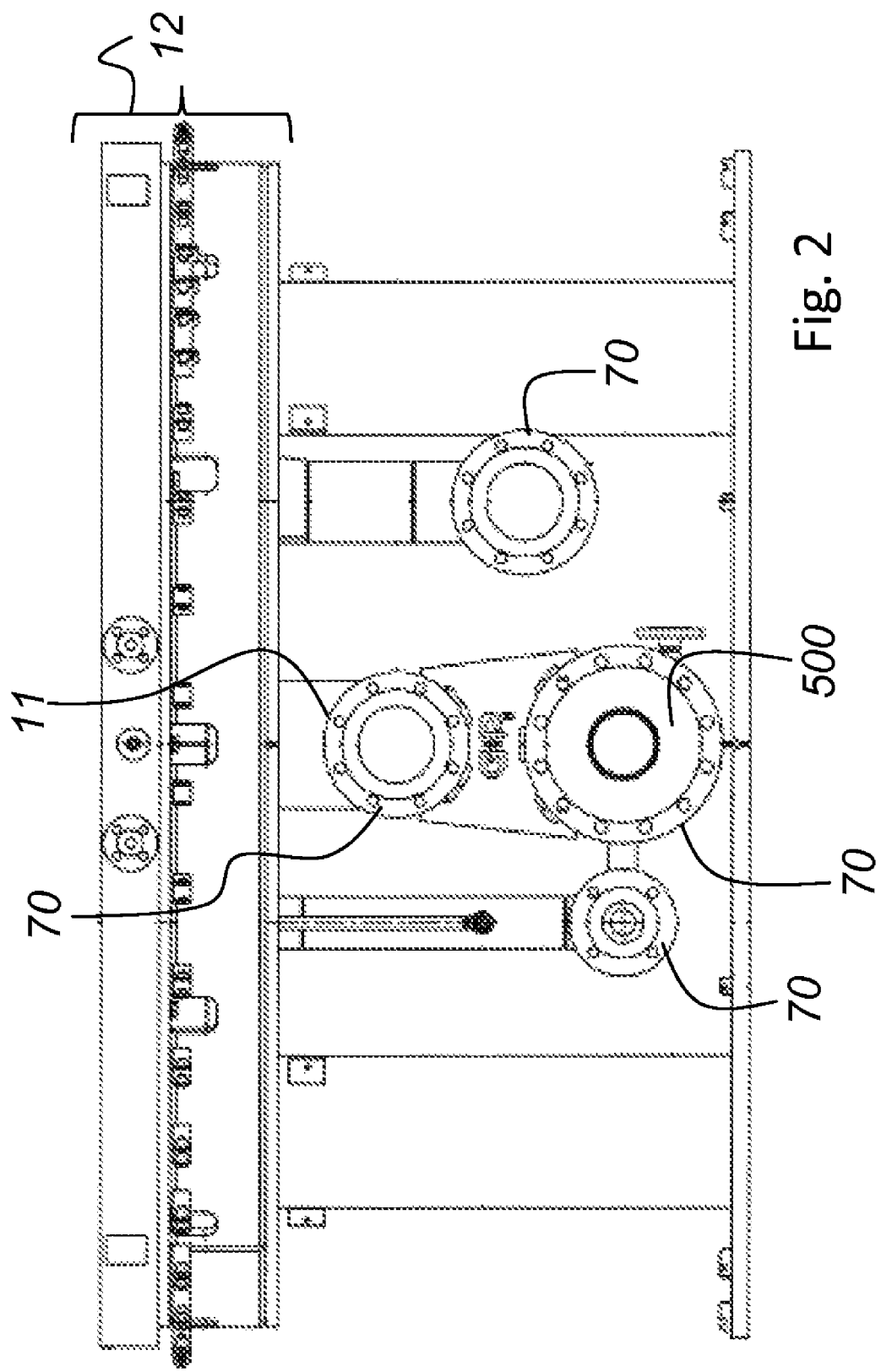
FIG. 2 shows a lateral view of the reactor base, in which one looks onto the inlet pipes and outlet pipes for the reactor.

FIG. 2 shows a partial view of the reactor base 12, wherein various pipes for feeding and discharging respectively are arranged from the base upwards. The feeding pipe 500 for fresh reaction gas is provided with a flange 70. Thus it is possible, that the pipe can be extended with a further section (not shown), in order to built up the system, which can consist of several reactors 10, and to provide each reactor 10 with the respective necessary gas for the reaction for the production of polycrystalline silicon. Likewise, an outlet pipe 11 for the mixture of gases from the reactor 10 is provided underneath the reactor base 12. This mixture of gases is abstracted during the reaction within the reactor 10 and is fed to a further processing station. A flange 70 is also provided here, onto which a further pipe section (not shown) can be attached to, in order to discharge the not abstracted reaction products as a mixture of gases and fed them to a further processing station.

FIG. 3 shows a lateral view of the reactor base 12. In the embodiment shown, the reactor base 12 comprises a first wall 31 and a second wall 32, which define a clearance. A cooling liquid is inserted into the clearance 34. The first wall 31 separates the clearance 34 against the interior space 110. The reactor base 12 carries a plurality of nozzles 400, through which the siliceous gas for the separation of polycrystalline silicon is distributed in the interior space 110 of the reactor 10. A pipe 500 is provided for the provision of the reaction gas, wherein said pipe 500 is provided with a respective flange 70. As already mentioned, an outlet pipe 21 for the mixture of gases is provided in the reactor base 12, which discharges the not abstracted reaction products of the separation of polycrystalline silicon on the filament rods 60 in the interior space 110 of the reactor. As already mentioned, the outlet pipe 21 is also provided with a flange 70. A further pipe can be attached to this flange 70 in order to provide for the discharge of the reaction gases.

FIG. 4 shows a top view onto the flange-like device 80, which is placed between a fist pipe section 11a, 21a or 41a and a second pipe section 11b, 21b or 41b of the pipe system 11, 21 or 41. With said flange-like device 80 specimens to be measured of the gas flow can be withdrawn from the gas flow by means of a sampling element 82 via the pipe section 81. The gas flow is shown in FIG. 4 in such a way that it proceeds into the second level. The sampling element 82 is designed as a pipe and provided with a circular cross-section $Q_{82}$, which is significantly smaller than the cross-section $Q_{81}$ of the pipe section 81, in which the mixture of gases, which contains different products, is transported. The flange-like device 80 is likewise provided on both sides with flanges 71. Therewith, the device 80 can be mounted on a flange 70 of the respective first or second pipe section 11a, 11b, 21a, 21b or 41a, 41b, which carries the gas for the monosilane process.

FIG. 5 shows a lateral view of the device 80. Thereby, the device 80 is a pipe-like section, from where a pipe 83 leads out of. This pipe 83 serves for the removal of a part of the mixture of gases carried in the pipe section 81 of the device 80. The device 80 is provided on both sides with a flange 70, 71. These flanges 71 of the device 80 operate together with respective flanges 70 of the first or second pipe section 11a, 11b, 21a, 21b or 41a, 41b, which carry the respective mixture of gases for the process for the production of monosilane.

Figure 6:
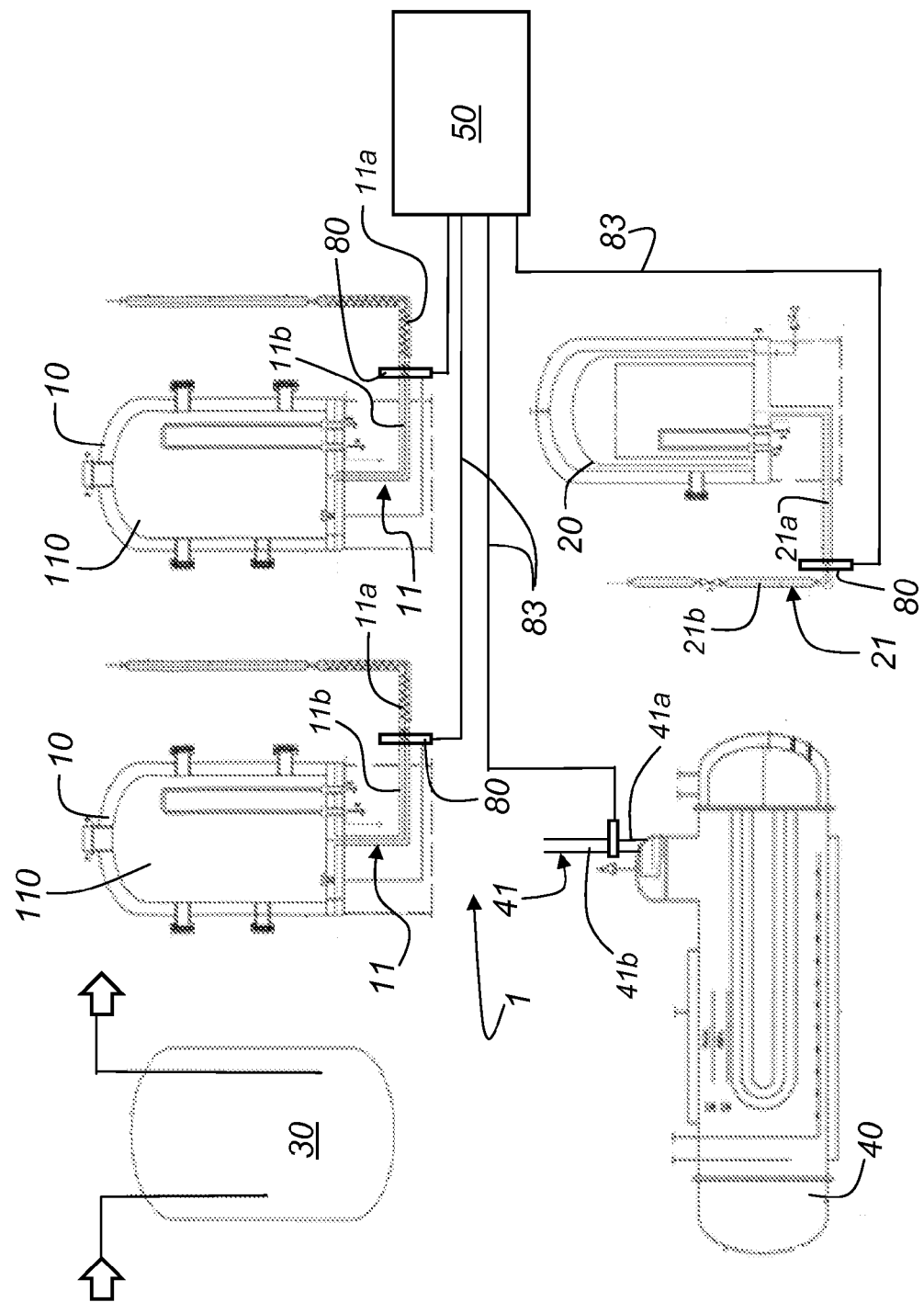
FIG. 6 shows a schematic assembly of a system for the production of polycrystalline silicon, wherein the devices according to the invention for withdrawing the samples are placed in the outlet pipes.

FIG. 6 shows the schematic construction of a system 1 for the production of polycrystalline silicon according to the monosilane process. The system 1 consists of at least one reactor 10, in which the polycrystalline silicon is deposited from a respective mixture of gases. Furthermore, a converter 20 is provided with the system 1, and said converter 20 is likewise provided with a fresh mixture of gases of tetrachlorosilane and hydrogen. Abstracted gas, which consists of tetrachlorosilane and hydrogen, is fed from the converter 20 to a vaporizer 40. In addition, an injection tank 30 is provided with the system 1, which contains trichlorosilane. This trichlorosilane is lead to the reactors 10 under admixture of hydrogen and other gases. As already mentioned, the reactor 10 is provided with an outlet pipe 11 for the mixture of gases from the interior space 110 of the reactor. Likewise, the converter 20 is provided with an outlet pipe 21 for the mixture of gases from the interior space of the converter 20. The vaporizer 40 is also provided with an outlet pipe 41 for the mixture of gases, which is composed in the vaporizer 40. The outlet pipe 11 of the reactor 10 consists of a first pipe section 11a and a second pipe section 11b. Both pipe sections 11a and 11b are connected together by means of flanges 70, 71. Likewise, the outlet pipe 21 of the converter 20 consists of a first pipe section 21a and a second pipe section 21b. Here, too, the two pipe sections 21a and 21b are connected together with two flanges 70, 71 in each case. In the same way, the outlet pipe 41 of the vaporizer consists of a first pipe section 41a and a second pipe section 41b, which are also connected together via two flanges 70, 71. In order that the device 80 is possible for the discharge of the reaction products from the outlet pipes 11, 21 and 41, the flanges 70, 71, which connect the pipe sections 11a, 11b or 21a and 21b, or 41a and 41b together, can be separated and the device 80 set in. The device 80 is provided with the sampling element 82, as described in FIGS. 4 and 5. The flange-like device 80 is provided in each case with a pipe 83, which leads to a gas-phase chromatograph 50. These pipes 83 are heated, so that the withdrawn gas and the withdrawn sampling to be measured respectively have the same temperature like the one which they had when they were withdrawn at the sampling station. The flange-like device 80 is thereby narrow in such a way that the installation is possible without big conversion of a system 1 for the production of polycrystalline silicon. Thereby, it is only necessary to separate the individual pipe section at the flanges and to insert the flange-like device 80. Finally, the flanges 70 of the pipe sections 11a, 11b, 21a, 21b, 41a, 41b are directly connected on both sides with the flange-like device 80.

While this invention has been particularly shown and described with references to preferred embodiments thereof, it will be understood by those skilled in the art that various changes in form and details may be made therein without departing from the scope of the invention encompassed by the appended claims.

What is claimed is:

1. An apparatus for extracting gaseous specimens to be measured from a production process for polycrystalline silicon, comprising:
   at least one reactor;
   a pipe system for feeding and/or discharging the at least one reactor with reaction gas, wherein the pipe system has at least a first pipe section and a second pipe section;
   a flange connecting the first pipe section and the second pipe section,
      wherein a reaction gas flows through the flange between the first pipe section and the second pipe section of the pipe system;
   a sampling element inserted between the pipe sections inside the flange,
      wherein a cross section of the sampling element is significantly smaller than a cross section of the pipe section; and
   a heated pipe from the sampling element.

2. The apparatus of claim 1, wherein the pipe from of the sampling element is connected with a gas-phase chromatograph.

3. The apparatus of claim 1, wherein the flange connects the first pipe section and the second pipe section of at least one converter, at least one injection tank, and/or at least one vaporizer.

* * * * *